United States Patent
Wei et al.

(10) Patent No.: US 6,350,990 B1
(45) Date of Patent: Feb. 26, 2002

(54) END CAP AND SEALING METHOD FOR IMAGER

(75) Inventors: Ching-Yeu Wei, Niskayuna; Michael Clement DeJule, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/433,754

(22) Filed: Nov. 4, 1999

(51) Int. Cl.⁷ .............................. G01T 7/00; G01T 1/20; H01L 31/0203

(52) U.S. Cl. ................................................ 250/370.11

(58) Field of Search ...................... 250/370.11, 370.08, 250/370.09

(56) References Cited

U.S. PATENT DOCUMENTS

| 5,389,775 | A |   | 2/1995 | Kwasnick et al. |
| 5,707,880 | A | * | 1/1998 | Aftergut et al. ................. 437/3 |
| 6,121,620 | A | * | 9/2000 | Tashiro et al. ......... 250/370.11 |
| 6,172,371 | B1 | * | 1/2001 | DeJule et al. .......... 250/370.11 |
| 6,262,422 | B1 | * | 7/2001 | Homme et al. ........ 250/370.11 |

* cited by examiner

*Primary Examiner*—Constantine Hannaher
*Assistant Examiner*—Albert Gagliardi
(74) *Attorney, Agent, or Firm*—Donald S. Ingraham; Christian G. Cabou

(57) ABSTRACT

An imager includes a substrate, a light-sensitive imaging array on the substrate, a scintillator over the array, and a cover over the scintillator sealed to the substrate. An edge of the array is situated close to an edge of the substrate relative to other edges of the array and substrate. A U-shaped end cap is sealed to and covers an edge of the cover, the edge of the substrate and a portion of each of the cover and substrate inward from their respective edges.

15 Claims, 2 Drawing Sheets

END CAP AND SEALING METHOD FOR IMAGER

BACKGROUND OF THE INVENTION

The present invention generally relates to imagers having an array of light-sensitive imaging elements. More particularly, the present invention relates to imagers with such an array positioned close to an edge of an underlying substrate relative to the other edges of the array and substrate.

For some imaging applications, the location of an active area of an imaging array relative to what is being imaged is important. For example, in medical applications such as mammography, current U.S. federal regulations state that the distance between the chest wall of the patient and the active imaging area must be no more than 6 mm, while German regulations currently require no more than 4 mm. At the same time, companies manufacturing such imaging equipment are concerned about the useful life of the imagers. Such spacing limitations can create physical limitations for components of the imager, affecting its useful life.

For example, a scintillator used to emit visible light in response to radiation and placed over a light-sensitive imaging array is sealed beneath a cover to prevent damage to the scintillator from such things as moisture in the air. However, due to the placement of the array and the space taken by the external housing, there is insufficient area for a proper sealant thickness. While it is possible to fit a thin line of sealant, such a thin line may be insufficient to prevent diffusion of moisture for any appreciable amount of time, since the time for degradation of the sealant is related to its width.

SUMMARY OF THE INVENTION

The present invention provides an imager having a substrate, an array of light-sensitive imaging elements on the substrate, a scintillator over the array, and a cover over the scintillator sealed to the substrate around a periphery of the cover. At least one edge of the array is situated closer to a respective edge of the substrate relative to other edges of the array and substrate. The imager also includes an end cap sealed to and covering the edge of the cover, the edge of the substrate, and a portion of each of the cover and substrate inward from their respective edges.

The present invention also provides a method of sealing an imager. The method includes sealing a cover for the scintillator to the substrate around a periphery of the cover, and sealing the edge of the cover, the edge of the substrate, and a portion of each of the cover and substrate inward from their respective edges with an end cap.

DETAILED DESCRIPTION OF THE INVENTION

Figure 1:
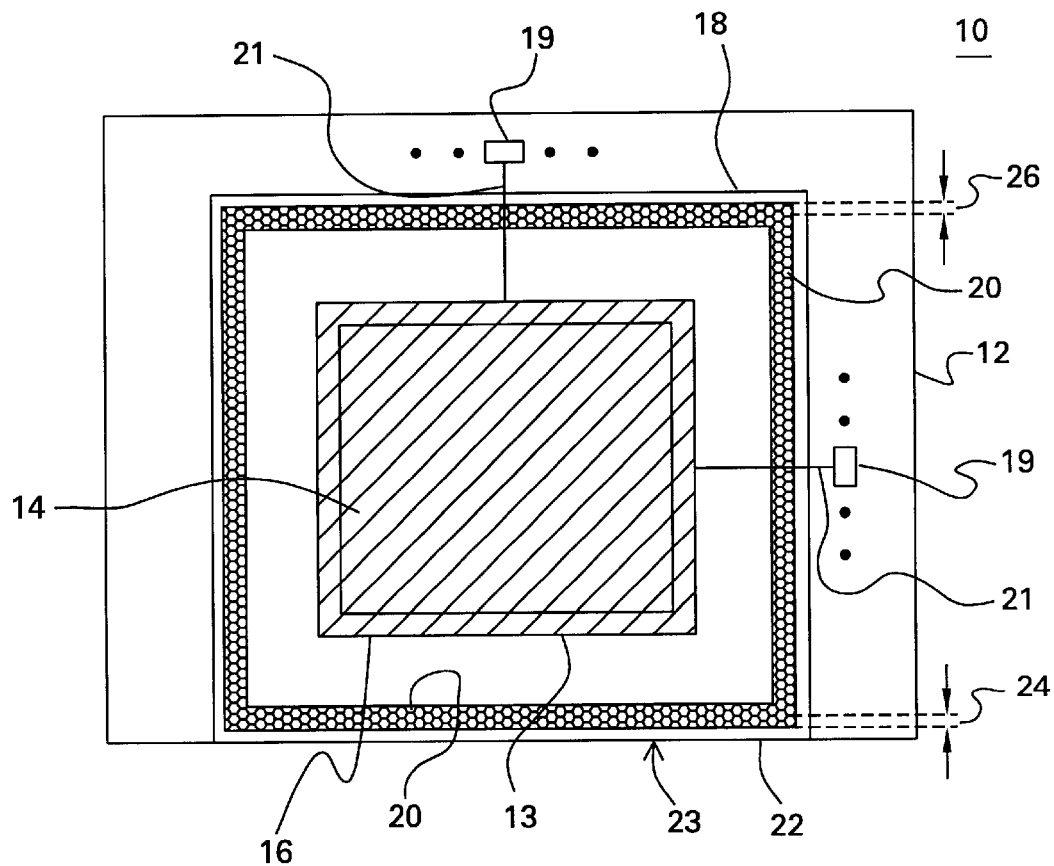
FIG. 1 is a plan view of an exemplary imager during fabrication, in accordance with the present invention.

FIG. 1 is a plan view of an exemplary imager 10 during fabrication. The imager may, for example, be intended for medical purposes (e.g., mammography). The imager includes a substrate 12 which typically comprises glass. On the substrate is an array 14 of light-sensitive imaging elements, which is also referred to as the "active" area. Depending on the pixel and array sizes, the array typically includes several million (e.g., 1–4 million) light-sensitive imaging elements, such as, for example, photodiodes. In addition, each light-sensitive imaging element typically has a corresponding switching device, such as, for example, a thin-film transistor (TFT). Over the array is a scintillator 16. As one skilled in the art will know, a scintillator emits visible light in response to incident radiation. For example, an x-ray scintillator comprising, for example, cesium iodide, emits visible light in response to x-ray energy.

In addition, commonly there are layers of material between the array and the scintillator. For example, there might be a barrier layer (not shown) to protect the array, comprising, for example, silicon nitride, or a combination of silicon oxide and silicon nitride. A cover 18 for the scintillator is sealed to substrate 12 around its periphery with a sealant 20, such as, for example, an epoxy. Cover 18 comprises, for example, carbon, or other x-ray transmissive material, or combinations thereof, and provides protection for the scintillator against exposure to ambient conditions.

The array 14 is addressed around its perimeter by a plurality of row and column address lines having contact pads 19, which are located along the sides of array 14 as indicated by the dot representation of FIG. 1. In operation, the voltage on the row address lines, and hence the TFTs, are switched on in turn, allowing the charge on that scanned line's photodiodes to be read out via the column address lines. The row address lines are commonly called the scan lines and the column address lines the data lines. The address lines are disposed in the active region of array 14, with contact fingers 21 extending from the active region towards the edge of the substrate. The contact fingers electrically connect to the contact pads which, in turn, can be electrically connected to external devices.

As shown in FIG. 1, a first close proximity array edge 13 of array 14 is situated closer to a first substrate edge 22 of substrate 12 than the other edges (e.g., the opposite edge and the adjoining edges disposed substantially at right angles to first substrate edge 22) of substrate 12. Similarly, portions of scintillator 16 and cover 18 overlying first close proximate array edge 13 are also situated closer to first substrate edge 22 than to the other edge of substrate 22. As this exemplary imager is for medical purposes, for example, mammography, it is relevant that current U.S. Federal regulations require the active array of the imager be disposed no more than 6 mm from the chest wall of the patient, while analogous regulations in Germany require the active array be disposed no more than 4 mm from the chest wall. The vicinity of edge 22 (ignoring any external housing) is where the imager is disposed most closely to the chest wall in the imaging process. This placement limitation poses practical problems for providing an effective seal between cover 18 and substrate 12. Along first edge 22 of substrate 12, cover first edge 23 (see FIG. 2) of cover 18 overlies substrate first edge 22. As used herein, "overlies" and the like refers to components being disposed such that the respective edges are substantially coextensive; no limitation on device orientation or operation is intended. Along cover first edge 23, the width 24 of sealant 20 is typically not greater than about 1 mm, while the other edges of cover 18 are not so limited and can accept sealant widths of 3 mm and more (e.g., sealant width 26 (FIG. 2)).

Figure 2:
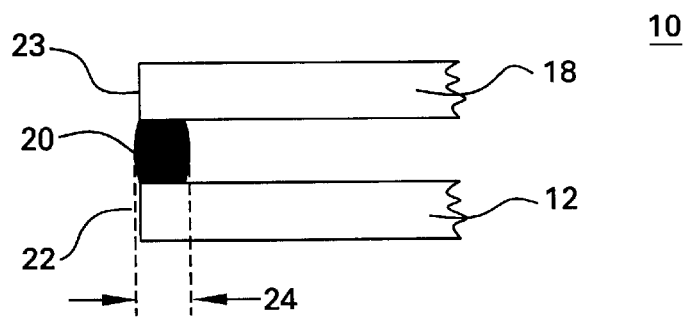
FIG. 2 is a simplified cross-sectional view of a relevant portion of the imager of FIG. 1 prior to sealing in accordance with the present invention.

FIG. 2 is a simplified cross-sectional view of the area of first substrate edge 22 and first cover edge 23 from FIG. 1. The narrowest (e.g. dimension 24) sealant width at any point around the periphery of the cover will determine maximum time the sealant will resist diffusion through the sealant. Thus, it is the narrowest sealant width that will determine the useful life of the imager, absent other factors that may shorten the imager's useful life, such as other component failures or physical damage to the imager. Useful life of an imager is compromised by exposure of components to ambient conditions, e.g., for a scintillator comprising cesium iodide, moisture in the air will quickly degrade its functionality.

Figure 3:
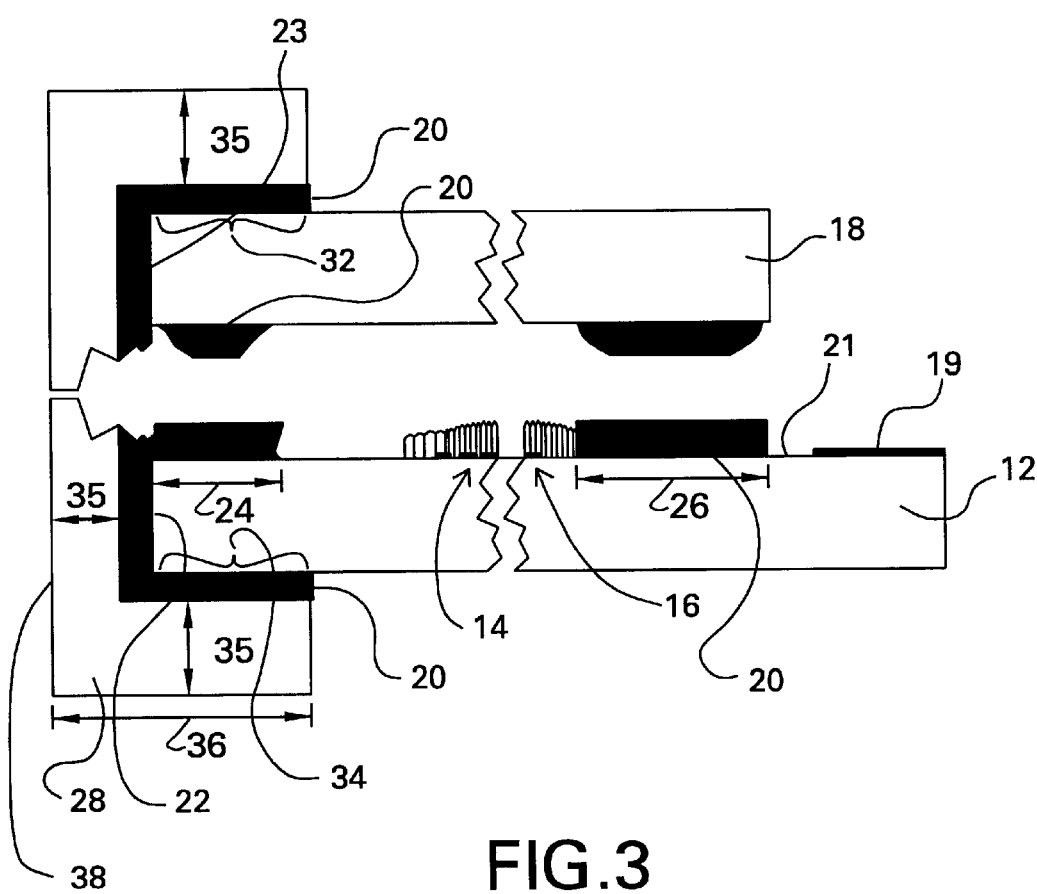
FIG. 3 shows the portion of FIG. 2 in more detail after sealing in accordance with the present invention.

FIG. 3 is a detailed cross-sectional view of the area of edges 22, 23 from FIG. 2 after the sealing of end cap 28 thereover. The end cap typically is U-shaped and comprises a metal, and where the imager is used for medical applications, the end cap preferably comprises a metal with a relatively low thermal coefficient of expansion (TCE), for example, a metal alloy of about 29% nickel, about 18% cobalt and about 53% iron. One example of such a metal alloy is commercially available under the trade name KOVAR. In addition, the end cap may be coated to prevent rust, for example, coated with a nickel plating. As shown, end cap 28 is disposed around and is sealed to first edge 22 of substrate 12, and to corresponding first edge 23 of cover 18, and to sealing contact portions 32 and 34 of the cover and substrate, respectively. Also, assuming the 4 mm regulation is applicable, end cap 28 typically has a thickness 35 of about ¼ mm thick. Sealant 20 (e.g., epoxy) is disposed between end cap 28 and the cover 18 and substrate 12. To meet the 4 mm regulation, the sealant for the end cap typically is about ¼ mm thick. Given these exemplary dimensions, the end cap results in the active area of array 14 being disposed a distance 36 of about 2 mm from the outer edge 38 of the end cap. This spacing leaves about 2 mm for the outer housing (not shown). The length of the area of the end cap 28 filled with sealant 20 also limits the rate of moisture diffusion through sealant 20 during the useful life of the imager.

One example of how the sealing with the end cap can be done will now be provided. The sealant is first dispensed into the U-shaped end cap and vertically aligned with ends 23 and 22 of the cover and substrate, respectively. Keeping the open portion of the end cap oriented in an upwards direction during sealing helps ensure even dispersion of sealant. The entire imager is then gently lowered into the wet sealant in the cap, and held there for curing. The sealant is then cured, for example, epoxy is cured at room temperature.

While several aspects of the present invention have been described and depicted herein, alternative aspects may be effected by those skilled in the art. For example, the end cap could be made of any material that approaches the TCE of the substrate and cover, bonds well to the sealant used, and acts as a moisture barrier. One example of a material other than metal that could be used for the end cap includes ceramic. As another example of alternative aspects, sealants other than epoxy could be used, so long as they are moisture resistant. Examples of other sealants include thermal setting polymers, thermally cured epoxy, and photo cured epoxy. Accordingly, it is intended by the appended claims to cover all such alternative aspects as fall within the true spirit and scope of the invention.

What is claimed is:

1. An imager, including:
    a substrate;
    an array of light-sensitive imaging elements on the substrate, wherein a first edge of the array is disposed closer to a first edge of the substrate relative to other edges of the array and substrate;
    a scintillator disposed over the array;
    a cover disposed over the scintillator and sealed to the substrate around a periphery of the cover; and
    an end cap sealed to and covering said first edge of the cover, a first edge of the substrate and a portion of each of the cover and substrate inward from said respective first edges.

2. The imager of claim 1, wherein the end cap is U-shaped.

3. The imager of claim 2, wherein a sealant used to seal the end cap is dispersed throughout an interior of the U-shaped end cap after sealing.

4. The imager of claim 1, wherein the end cap comprises a metal alloy.

5. The imager of claim 1, wherein the cover and end cap are sealed with an epoxy.

6. An imager, including:
    a substrate;
    a photodiode array on the substrate, wherein a first edge of the photodiode array is situated closer to a first edge of the substrate relative to other edges of the photodiode array and substrate;
    a scintillator over the array;
    a cover over the scintillator sealed to the substrate around a periphery of the cover with an epoxy; and
    a U-shaped end cap sealed with the epoxy to and covering a first edge of the cover, the first edge of the substrate and a portion of each of the cover and substrate inward from their respective edges.

7. The imager of claim 6, wherein the cover comprises carbon, or other suitable x-ray transmissive material, or combinations thereof.

8. The imager of claim 6, wherein the U-shaped end cap comprises a metal alloy of nickel, cobalt and iron.

9. The imager of claim 6, wherein the U-shaped end cap has a thickness of about ¼ mm.

10. The imager of claim 6, wherein the portion of each of the cover and substrate is less than about 1.5 mm.

11. The imager of claim 6, wherein the scintillator comprises cesium iodide.

12. A method of sealing an imager, the imager including a substrate, an array of light-sensitive imaging elements on the substrate, a first edge of the array being situated closer to a first edge of the substrate relative to other edges of the array and substrate, and a scintillator over the array, the method including:
    sealing a cover for the scintillator to the substrate around a periphery of the cover; and
    sealing an edge of the cover, the edge of the substrate, and a portion of each of the cover and substrate inward from their respective edges with an end cap.

13. The method of claim 12, wherein sealing the cover and sealing with the end cap each include applying an epoxy.

14. The method of claim 12, wherein sealing with the end cap includes sealing with a U-shaped end cap.

15. A method of sealing an imager, including:
    providing an imager including a substrate, a photodiode array on the substrate, an edge of the array being situated close to an edge of the substrate relative to other edges of the array and substrate, and a scintillator over the array;
    sealing a cover for the scintillator to the substrate around a periphery of the cover with an epoxy; and
    sealing with an epoxy an edge of the cover, the edge of the substrate, and a portion of each of the cover and substrate inward from their respective edges with an end cap.

* * * * *